US008873170B2

(12) United States Patent
Patil et al.

(10) Patent No.: US 8,873,170 B2
(45) Date of Patent: Oct. 28, 2014

(54) REPLACEMENT LENS CARTRIDGE

(71) Applicant: Honeywell International Inc., Morristown, NJ (US)

(72) Inventors: Swapnil Gopal Patil, Maharashtra (IN); Joseph Rodrigues, Cranston, RI (US); Joseph Venagro, Cranston, RI (US); Felix Gauthier, Montreal (CA); Marc LaMontagne, Repentigny (CA); Bach Dang Duc, Brossard (CA)

(73) Assignee: Honeywell International Inc., Morristown, NJ (US)

( * ) Notice: Subject to any disclaimer, the term of this patent is extended or adjusted under 35 U.S.C. 154(b) by 31 days.

(21) Appl. No.: 13/683,661

(22) Filed: Nov. 21, 2012

(65) Prior Publication Data

US 2013/0081615 A1 Apr. 4, 2013

Related U.S. Application Data

(63) Continuation-in-part of application No. PCT/US2011/044229, filed on Jul. 15, 2011, and a continuation-in-part of application No. 13/683,013, filed on Nov. 21, 2012.

(60) Provisional application No. 61/365,149, filed on Jul. 16, 2010, provisional application No. 61/465,422, filed on Mar. 18, 2011.

(51) Int. Cl.

| | |
|---|---|
| ***G02B 7/02*** | (2006.01) |
| ***G02B 23/16*** | (2006.01) |
| ***A42B 1/08*** | (2006.01) |
| ***A61F 9/02*** | (2006.01) |

(52) U.S. Cl.

USPC ........... 359/819; 359/811; 359/507; 359/513; 2/424; 2/434

(58) Field of Classification Search

USPC ......... 359/811, 819, 350, 360, 361, 481, 507, 359/513; 2/173, 224–229, 431, 434, 435

See application file for complete search history.

(56) References Cited

U.S. PATENT DOCUMENTS 3,945,044 A 3/1976 McGee et al.
3,963,021 A 6/1976 Bancroft
4,076,373 A * 2/1978 Moretti ........................ 359/507
(Continued)

FOREIGN PATENT DOCUMENTS

EP 1810648 A1 7/2007
WO 9741815 11/1997

OTHER PUBLICATIONS

PCT/US2011/044229; International Preliminary Report on Patentability and Written Opinion; Jan. 22, 2013; 6 pages.

*Primary Examiner* — Loha Ben
(74) *Attorney, Agent, or Firm* — Conley Rose, P.C.; Kristin Jordan Harkins

(57) ABSTRACT

Embodiments relate generally to a replaceable lens cartridge for use with a face mask, for example a respirator. The cartridge comprises a plurality of molded lenses, each lens sized to extend over one or more eyes of a wearer and typically having a curved shape and a plurality of catches; and a molded carrier mounting the lenses in stacked arrangement, the carrier having a first set of catches receiving the catches on one of the lenses.

20 Claims, 21 Drawing Sheets

(56) References Cited

U.S. PATENT DOCUMENTS

| | | | |
|---|---|---|---|
| 4,149,276 A | 4/1979 | Castro | |
| 4,542,538 A | 9/1985 | Moretti et al. | |
| 4,563,065 A | 1/1986 | Kreissl | |
| 4,648,394 A | 3/1987 | Wise | |
| 4,748,697 A * | 6/1988 | Hodnett | 2/438 |
| 4,930,539 A | 6/1990 | van Rooy | |
| 4,989,598 A | 2/1991 | Berg et al. | |
| 5,163,185 A * | 11/1992 | Hodnett | 2/424 |
| 5,549,104 A | 8/1996 | Crump et al. | |
| 5,991,072 A * | 11/1999 | Solyntjes et al. | 359/361 |
| 6,102,033 A | 8/2000 | Baribeau et al. | |
| 7,133,222 B2 * | 11/2006 | Chintala et al. | 359/811 |
| 7,293,560 B2 | 11/2007 | Dahrendorf et al. | |
| 7,762,252 B2 | 7/2010 | Prete | |
| 7,975,688 B1 | 7/2011 | Truitt | |
| 8,028,695 B2 | 10/2011 | Acker et al. | |
| 8,176,913 B2 | 5/2012 | Ivory | |
| 2009/0194101 A1 | 8/2009 | Kenyon et al. | |
| 2009/0241965 A1 | 10/2009 | Sather et al. | |
| 2009/0266361 A1 | 10/2009 | Bilger et al. | |
| 2012/0137414 A1 * | 6/2012 | Saylor | 2/435 |
| 2012/0152255 A1 | 6/2012 | Barlow et al. | |

* cited by examiner

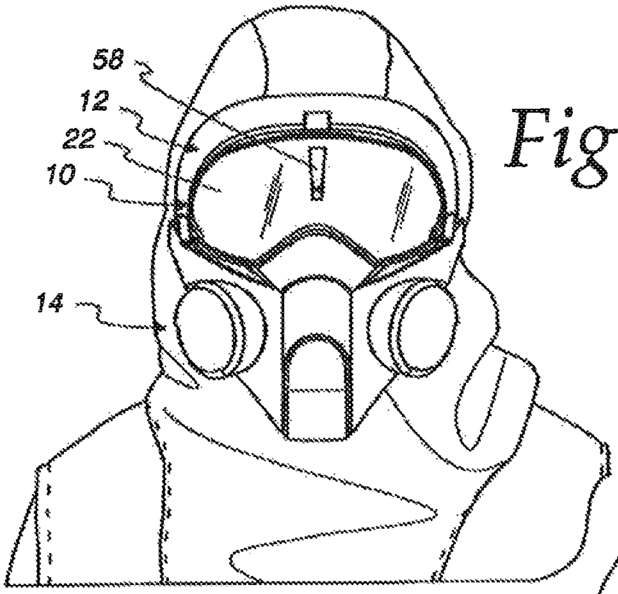
Fig. 23A
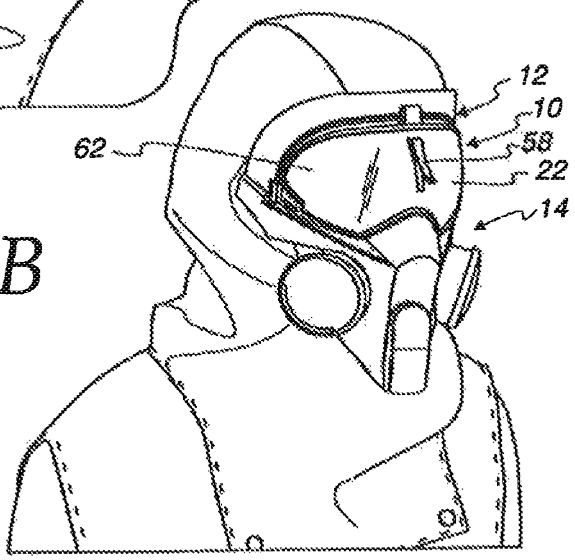
Fig. 23B
Fig. 24
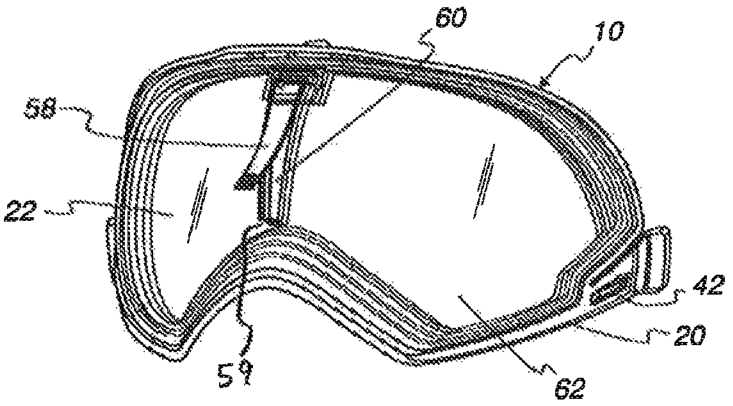

REPLACEMENT LENS CARTRIDGE

CROSS-REFERENCE TO RELATED APPLICATIONS

This application is a Continuation-in-Part of PCT application Ser. No. PCT/US2011/044229, filed Jul. 15, 2011 and entitled Replacement Lens Cartridge, which is related to and claims the benefit of the filing date of U.S. Provisional Patent Application Ser. No. 61/365,149, filed Jul. 16, 2010 and U.S. Provisional Patent Application Ser. No. 61/465,422, filed Mar. 18, 2011, all of which are hereby incorporated by reference as if reproduced in their entirety.

This application claims priority to India Provisional Application Serial No. 3292/DEL/2012, filed Oct. 25, 2012 in the India Patent Office and entitled "Replacement Lens Cartridge", hereby incorporated by reference as if reproduced in its entirety.

This application is a continuation in part of U.S. patent application Ser. No. 13/683,013, entitled "Abrasive Blast Respirator", filed Nov. 21, 2012 in the U.S. Patent Office, which is incorporated herein by reference in its entirety to the extent it does not conflict with this disclosure.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments may relate generally to replacement lens cartridges directed to protective face and eyewear such as might be worn in the shipyard industry, but might be suitable for different types of construction sites where, for example, sandblasting/shot blasting is performed.

BACKGROUND

In order to build or repair ships, workers often have to crawl and work in very tight space (vessel, portal, etc.) where their protective equipment (for example a respirator) is subjected to grit rebound. Those rebounds will damage the lens of their respirator and blur their vision. Also, workers currently use a respirator that typically only provides a 4½ inch×2¾ inch flat field of view. This tunnel vision adds to the claustrophobic effect of their work environment. Plus, it requires more head movement from the worker to see where he is aiming with the blasting gun. Workers would benefit from a larger field of vision. Disclosed embodiments seek to provide one or more improvements to help workers in their difficult field, for example.

SUMMARY

Aspects of the disclosure may include embodiments of a replaceable lens cartridge for use with a face mask comprising one or more of the following: a plurality of removable lenses; a carrier mounting the lenses in a stacked arrangement, wherein the stacked arrangement may comprise gaps between the lenses; and a plurality of gaskets located between the lenses in the stacked arrangement, wherein the gaskets may be operable to seal the gaps between the lenses. In an embodiment, the gaskets may comprise a shape corresponding approximately to an outline of the lenses and may be located in proximity to the edges of the lenses. In an embodiment, the gaskets may comprise an adhesive material that may attach securely to a back surface of a first lens and may seal to a front surface of a second lens. In an embodiment, the seal of the gaskets to the corresponding front surface of the second lens may be removable, such that when the first lens might be removed from the cartridge, the corresponding gasket that is attached to the back surface of the first lens may be completely removed as well and may remain attached to the back surface of the first lens. In an embodiment, when the first lens may be removed from the cartridge, the gasket may be completely removed from sealing with the front surface of the second lens, without leaving any portion of the gasket material on the front surface of the second lens. In an embodiment, each lens may comprise a plurality of catches and the carrier may comprise a corresponding plurality of catches to receive the catches of the lenses to form the stacked arrangement. In an embodiment, the plurality of catches on each lens may comprise at least four projections extending from the perimeter of the lens, and wherein the corresponding plurality of catches on the carrier may comprise a matching number of reliefs on the carrier, each relief receiving one of the projections.

In an embodiment, the carrier might further comprise a peripheral lip that may extend over perimeters of the lenses mounted in the stacked arrangement on the carrier, and the plurality of catches of the carrier may be formed in the peripheral lip of the carrier. In an embodiment, the carrier might further comprise a fixed lens underlying the lenses mounted in stacked arrangement on the carrier, and the lens cartridge might further comprise a gasket located behind the fixed lens operable to seal between the fixed lens of the carrier and the face mask. In an embodiment, the carrier might further comprise a plurality of mount catches for engagement with the face mask. In an embodiment, the face mask may comprise a base lens and the gasket located behind the fixed lens may seal between the fixed lens of the carrier and the base lens of the face mask. In an embodiment, the plurality of lenses and the fixed lens of the carrier may comprise a curved shape. In an embodiment, the curved shape of the lenses may allow for a field of vision of between about 100° and about 170°, and in an embodiment the gaskets may comprise a curved shape corresponding to the curved shape of the removable lenses and the fixed lens. In an embodiment, the plurality of lenses may be formed of molded polycarbonate plastic material.

Other aspects of the disclosure may include embodiments of a replaceable lens cartridge for use with a respirator face mask for use during blasting with grit comprising one or more of the following: a plurality of removable lenses formed of molded plastic; a carrier mounting the lenses in a stacked arrangement, wherein the stacked arrangement may comprise gaps between the lenses; and a plurality of gaskets located between the lenses in the stacked arrangement, wherein the gaskets may be operable to seal the gaps between the lenses sufficiently to prevent grit from entering between the lenses, wherein each gasket may comprise an adhesive material between a corresponding top lens and bottom lens, wherein the gasket may be affixed to a back surface of the top lens and may seal removably to a front surface of the bottom lens. In an embodiment, upon removal of the top lens from the cartridge, the corresponding gasket that may be attached to the back surface of the top lens may be completely removed and may remain affixed to the hack surface of the top lens, without leaving any significant portion of the gasket material on the front surface of the bottom lens. In an embodiment, the lens cartridge might further comprise a plurality of pull tabs, each tab corresponding to one of the lenses, wherein the tab may be centered on the lens and attached to the lens to allow for removal of the lens from the carrier when the tab is pulled, wherein each lens may include a recess underlying the pull tab to receive the pull tab and prevent unwanted interference between the pull tab and any adjacent lens. In an embodiment, the gaskets may comprise a shape corresponding approximately to a perimeter outline of the lenses which includes a notch to avoid interference with the pull tabs.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIGS. 23A-23B illustrate perspective views from the front of an alternate embodiment of an exemplary respirator and lens cartridge concept as worn by a worker with additional protective garments according to an embodiment of the disclosure;

FIG. 24 illustrates a perspective view from the front of the alternate embodiment of the lens cartridge and lenses of FIGS. 23A and 23B according to an embodiment of the disclosure;

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

According to one feature, a replacement lens cartridge 10 is made from molded plastic (for example, polycarbonate, TPU, acrylic, etc.), preferably suitable for optic purposes. Because of the process and material, the cartridge 10 offers a cost effective system compared to conventional products. Furthermore, the density of resins, such as polycarbonate, is half of the glass density which brings down the weight considerably in comparison to conventional products.

Figure 1:
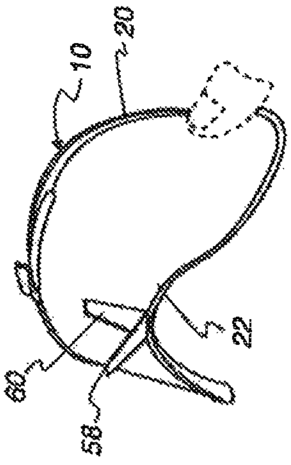
FIG. 1 illustrates a perspective view from the front and below of a lens cartridge according to an embodiment of the disclosure.
Figure 2:
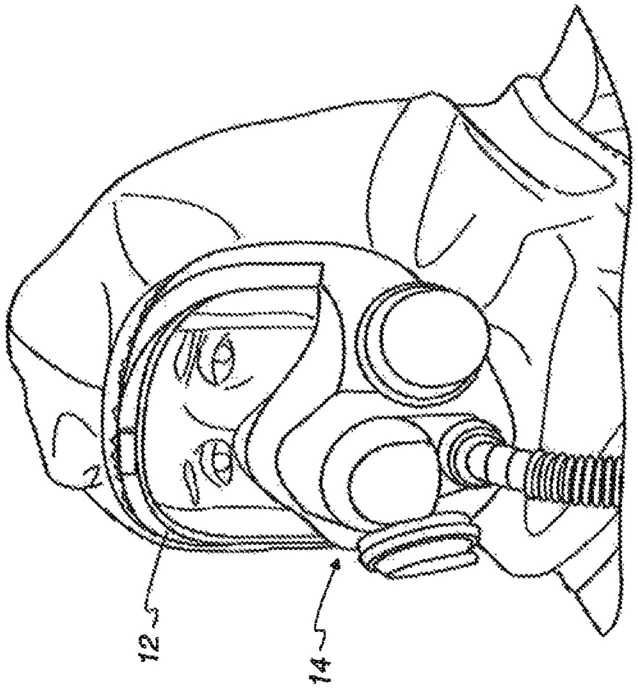
FIG. 2 illustrates a perspective view of an exemplary respirator for use with the lens cartridge and worn by a worker with additional protective garments according to an embodiment of the disclosure.
Figure 4:
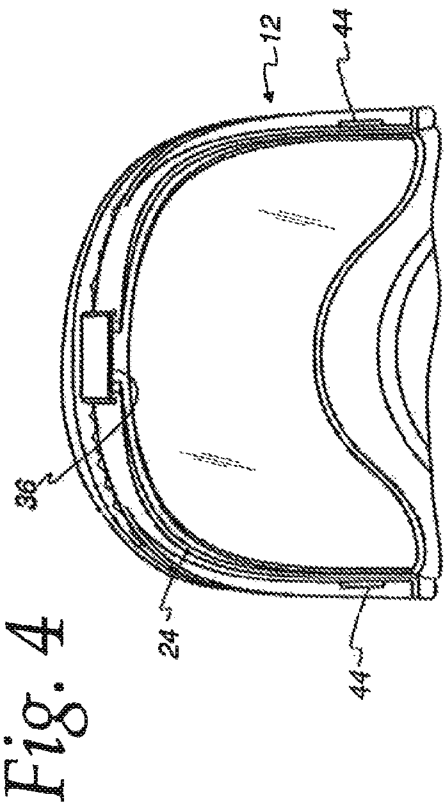
FIG. 4 illustrates an enlarged, front perspective view of a portion of the respirator of FIG. 2 according to an embodiment of the disclosure.
Figure 3:
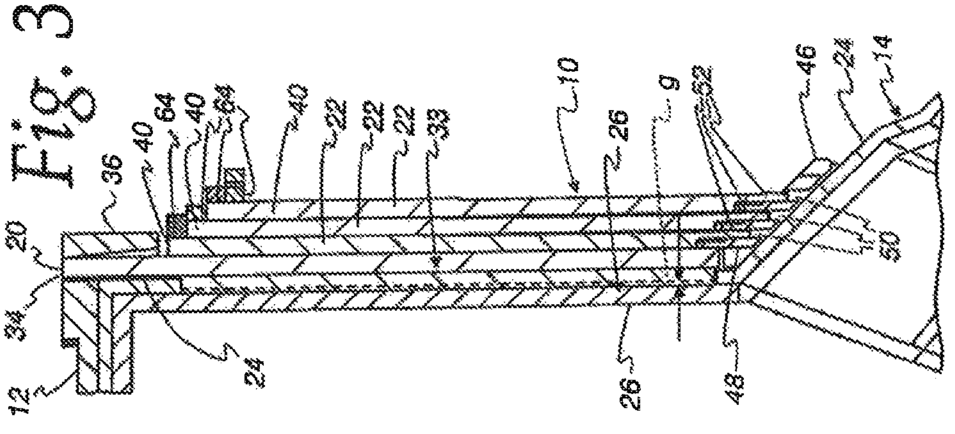
FIG. 3 illustrates a section view of the cartridge of FIG. 1 mounted on the respirator of FIG. 2 and taken along the centerline of the cartridge and respirator according to an embodiment of the disclosure.

With reference to FIGS. 1-3, the cartridge 10 is provided for use on a face mask of a respirator or other device having a permanent lens for protecting the eyes of a user, such as the face mask 12 of the respirator 14 shown in FIG. 2. The cartridge 10 comprises a carrier 20 and multiple (typically 3 or 4) disposable lenses 22. The cartridge 10 is preferably molded and is not limited to flat surfaces. Accordingly, each lens 22 can have a curved shape and, for example, can be a cylindrical lens, a spherical lens, or a tonic lens. With those curvatures, it's possible to offer more peripheral view. For example, in one embodiment, the curved shape of the lenses 22 may allow for a field of vision of between about 100° and about 170°, or in one exemplary embodiment, about 160°. In one embodiment, each lens 22 inside the carrier 20 is identical. However, if overwhelming distortion occurs by stacking the lenses 22, it would be possible to make each lens 22 slightly different to correct distortion made by the previous lens 22 in the cartridge 10.

Figure 5:
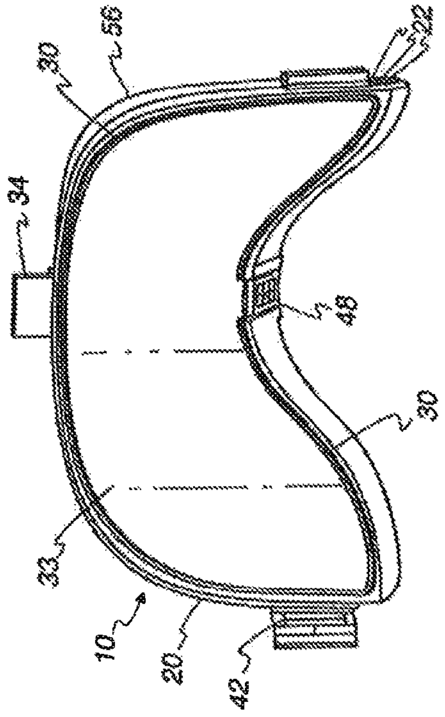
FIG. 5 illustrates a perspective view from the rear of the cartridge of FIG. 1 and showing an optional feature according to an embodiment of the disclosure.

As seen in FIG. 3, when the cartridge 10 is mounted on the respirator 14, it abuts a protective rubber 24 that covers a permanent lens 26 of the respirator 14. This will create a small gap g between the permanent lens 26 and the cartridge 10, which will allow proper assembly of the cartridge 10 on the respirator 14 even if grit is trapped between the two. As shown FIG. 5, another way to create the gap g is by adding a glued rubber cord 30 that follows the perimeter on the back surface 32 of the cartridge carrier 20. This structure can also be achieved by co-injection as well.

Figure 8A:
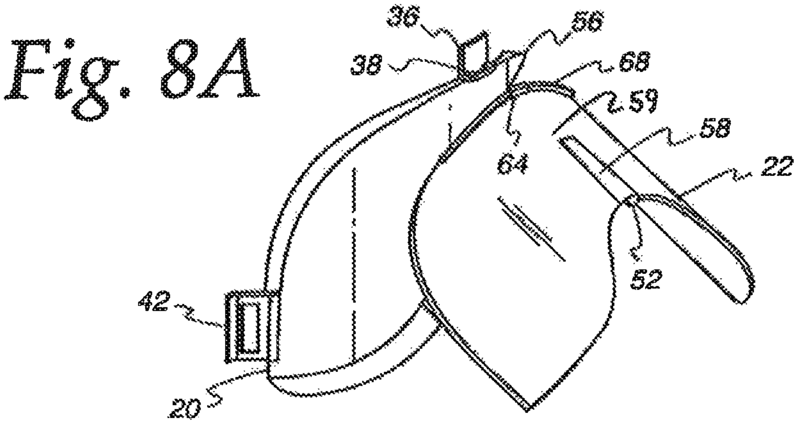
FIGS. 8A-8B illustrate front perspective views showing the carrier and lens of FIGS. 7A and 7B, with FIG. 8A showing the lens prior to engagement with the carrier and FIG. 8B showing the lens partially engaged with the carrier as it is inserted according to an embodiment of the disclosure.
Figure 8B:
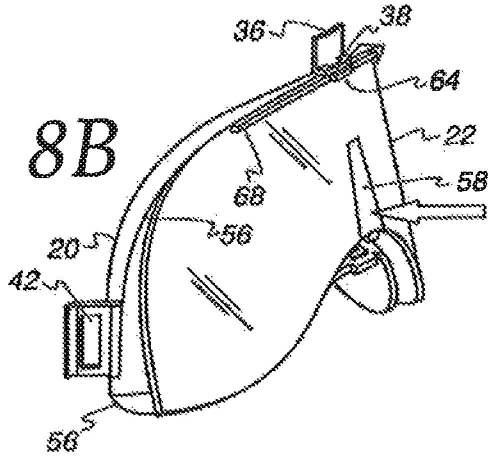

The carrier 20 holds the stack of lenses 22 together and provides means to attach the cartridge 10 on the respirator 14. Its also the last layer of protection of the cartridge 10 with a fixed lens 33. As best seen in FIGS. 6A-6G, the carrier 20 has a top tooth 34 that can be inserted into a face mask clamp or slot 36 on the face mask 12 of the respirator 14. Aligned with this top tooth 34, there is a catch in the form of a slot 38 (as shown in FIGS. 8A-8B) on the carrier 20 to receive a catch in the form of a lens top tooth 40 on the first loaded lens 22. There is hook or slot 42 on each side of the carrier 20 to secure the cartridge 10 on the respirator 14 by engagement with corresponding hook receiving tabs 44 on each side the face mask 12 of the respirator 14.

Figure 7A:
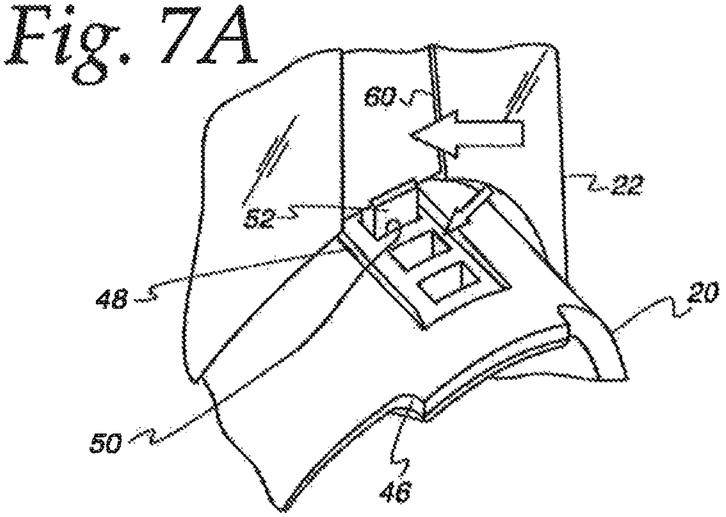
FIGS. 7A-7B illustrate broken, perspective views from the front and above showing a selected portion of a carrier of the cartridge and a lens carried in the cartridge, with FIG. 7A showing the lens being inserted and FIG. 7B showing the lens in an inserted position according to an embodiment of the disclosure.
Figure 7B:
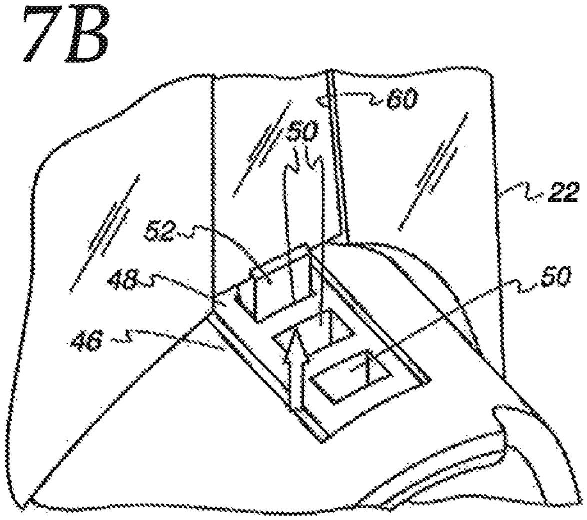

As best seen in FIGS. 3, 7A and 7B, the carrier 20 includes a bridge 46 that extends over the nose of a wearer and has a blade or tab 48 that has a set of catches in the form of openings 50 to receive a catch in the form of a bottom tooth 52 of each of the lenses 22. This blade 48 is cantilevered from the bridge 46 and will bend when each of the lenses 22 are inserted into the carrier 10, then move to its initial or as-molded position to secure the lenses 22 in place.

Figure 9:
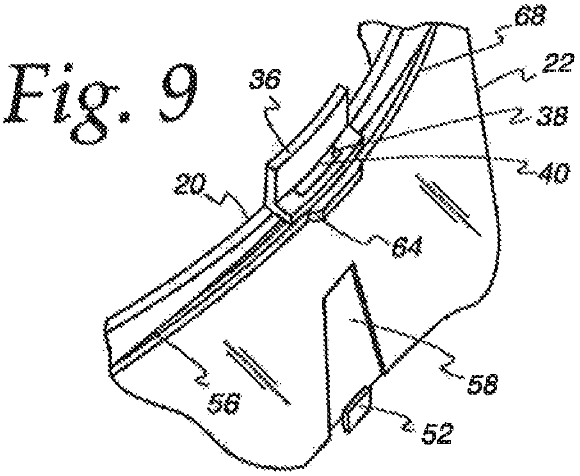
FIG. 9 illustrates an enlarged perspective front above and to the front showing the carrier and lens of FIGS. 7A, 7B, 8A and 8B according to an embodiment of the disclosure.

As best seen in FIGS. 8A-9, on the perimeter of the carrier 20 there is an extrusion or peripheral lip 56 that extends forward to protect the lens 22 from dust that could enter between each of the lenses 22. This peripheral lip 56 also helps to avoid lens shifting.

Figure 6A:
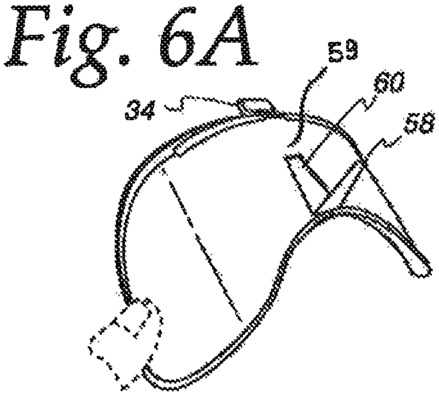
FIGS. 6A-6G illustrate a sequence of figures showing the steps for mounting and dismounting the cartridge of FIG. 1 onto the exemplary respirator of FIGS. 2 and 3, and for removing replacement lenses carried in the cartridge according to an embodiment of the disclosure.
Figure 6B:
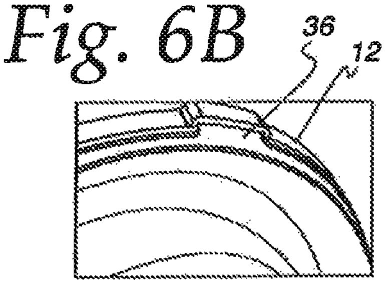
Figure 6C:
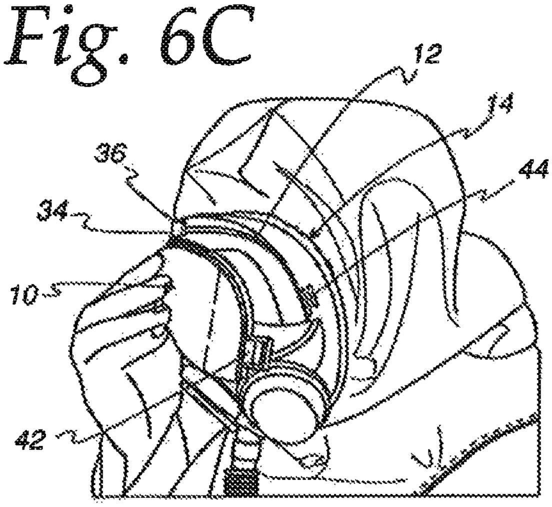
Figure 6D:
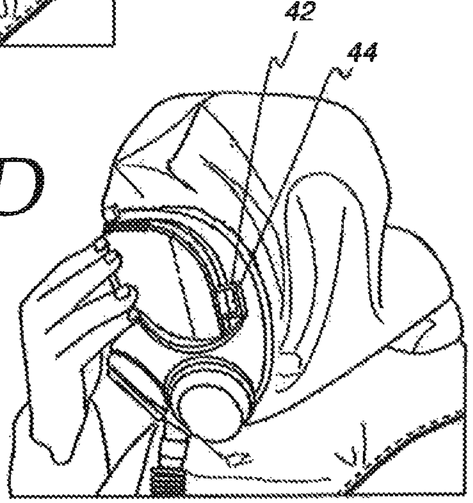
Figure 6E:
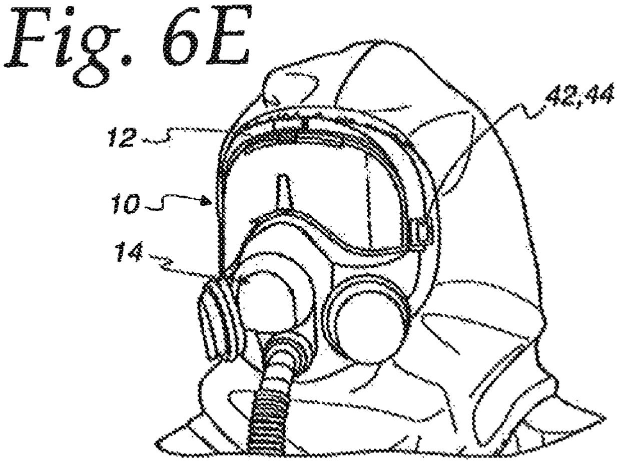
Figure 6F:
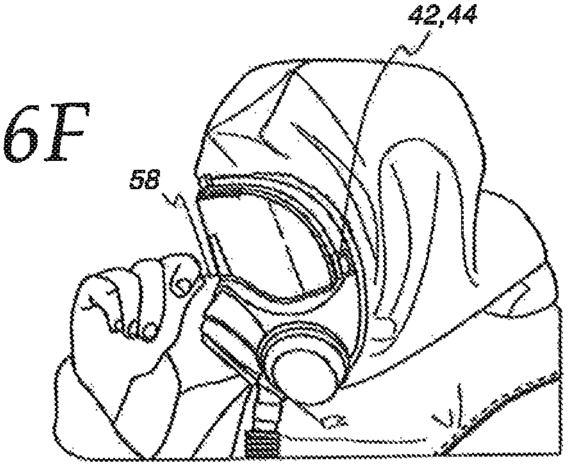
Figure 6G:
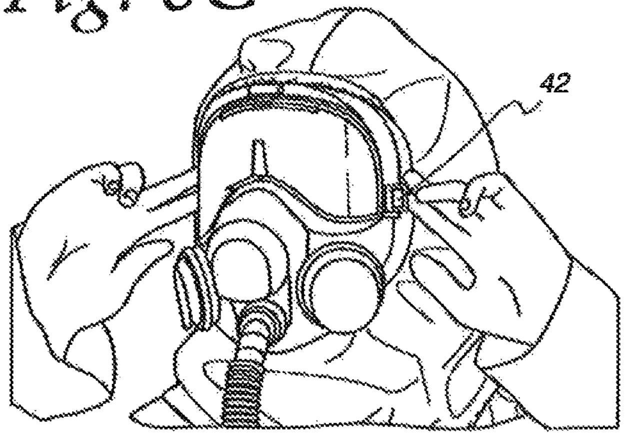

As best seen in FIGS. 1 and 6A, each lens 22 in the cartridge 10 has a transparent pull tab 58 centered on the lens 22 to overlie a nose bridge portion 59 of the lens 22 and attached to the lens 22 for removal of the used lens 22. This tab 58 could be over molded in the lens 22 or glued in a secondary operation. There is a recess 60 on the front surface 62 of the lenses 22 to receive the folded tab 58 to avoid any gaps between the lenses 22.

Figure 14:
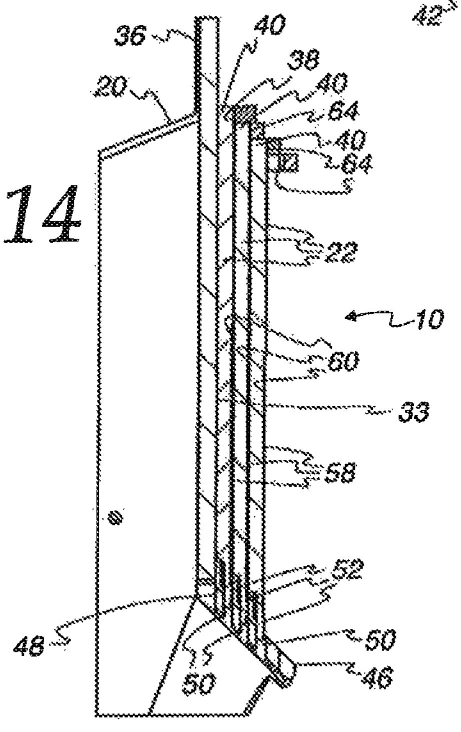
FIG. 14 illustrates a section view similar to FIG. 3 and taken along the line 14-14 in FIG. 12 according to an embodiment of the disclosure.

As best seen in FIGS. 9 and 14, each lens 22 has a top tooth 40 and a bottom tooth 52. As previously discussed, the top tooth 40 is made to align the first lens 22 in the carrier top slot 38. There is also a top slot 64 on each lens 22 to align the next lens 22 by receiving the top tooth 40 of the next lens 22. There is a forwardly projecting extrusion or lip 68 on the upper section of the each lens 22 to avoid shifting of the lenses 22 relative to each other.

Figure 10:
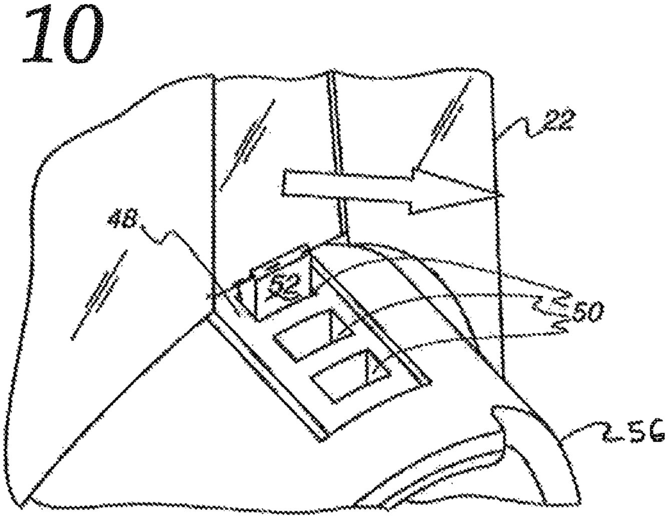
FIGS. 10 and 11 illustrate enlarged views of the carrier and lens shown in FIGS. 7A and 7B, with FIG. 10 showing one option for lens removal and FIG. 11 showing another option for lens removal according to embodiments of the disclosure.
Figure 11:
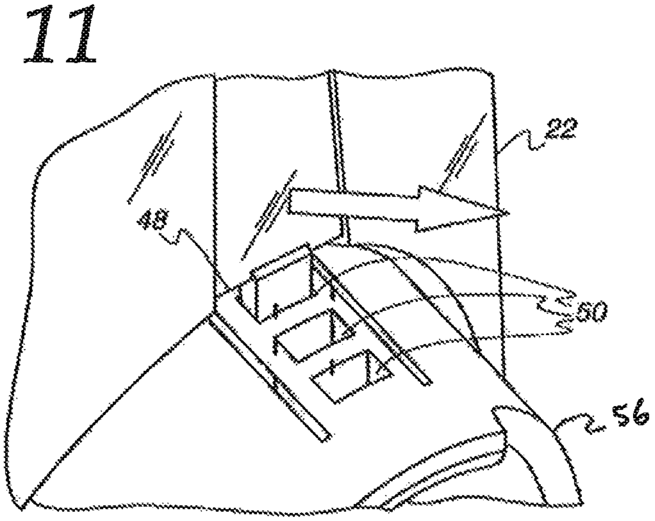

When the lenses 22 are placed into the carrier 20, the bottom tooth 52 on each lens 22 will snap into the blade 48 of the carrier bridge portion 46, with each lens 22 having its own opening 50 in the blade 48. As illustrated by the horizontal dashed lines in FIG. 10, in one embodiment, the bottom tooth 52 will break when the tab 58 is pulled, allowing for removal of the lens 22 (which may, for example, be desired when the lens 22 has become so damaged and/or scratched that the user can no longer sufficiently see through it). In the embodiment of FIG. 10, the bottom tooth 52 may be designed to break along the horizontal dashed line to allow for removal of the lens 22. In another embodiment, as illustrated by the vertical dashed lines in FIG. 11, a portion of the blade 48 on the bridge 46 may break instead of the lens bottom tooth 52. In the embodiment of FIG. 11, the side wall of the opening 50 (wherein the bottom tooth 52 of the lens 22 is held) may be designed to break when a certain force is applied by pulling the lens and therefore the tooth 52, allowing for removal of the bottom tooth 52 from the blade 48 and therefore lens 22.

Figure 12:
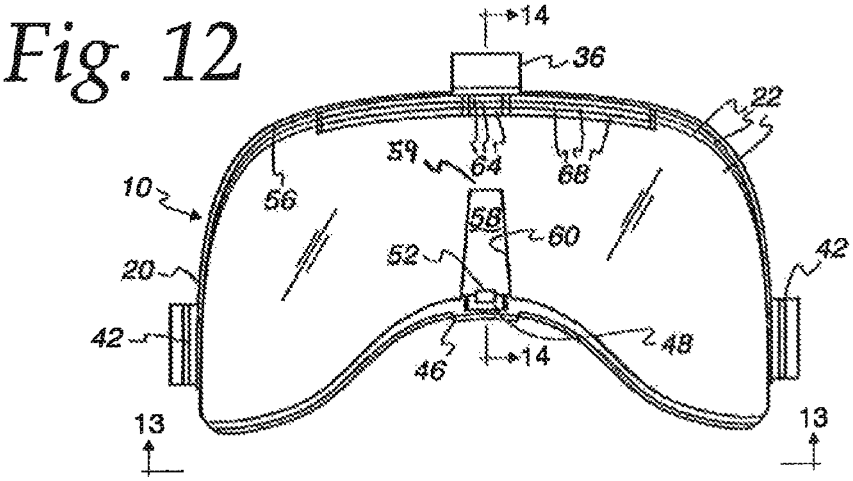
FIG. 12 illustrates a front view of the cartridge of FIG. 1 according to an embodiment of the disclosure.
Figure 13:
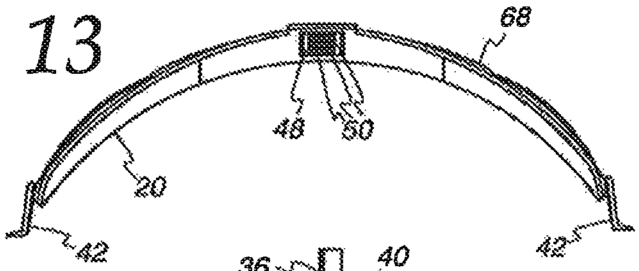
FIG. 13 illustrates a bottom view taken from line 13-13 in FIG. 12 according to an embodiment of the disclosure.
Figure 15:
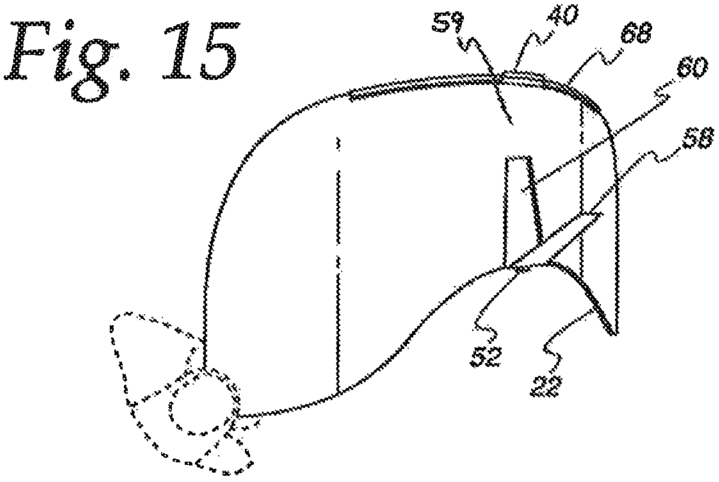
FIG. 15 illustrates a perspective view from the front and side of a replacement lens according to an embodiment of the disclosure.
Figure 16:
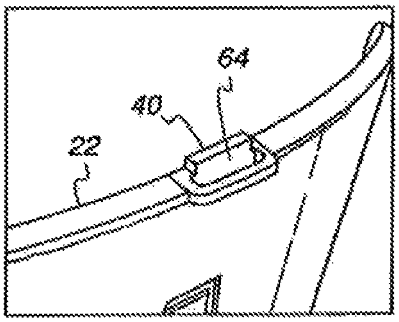
FIG. 16 illustrates a enlarged perspective view from above of a portion of the lens of FIG. 15 according to an embodiment of the disclosure.
Figure 17:
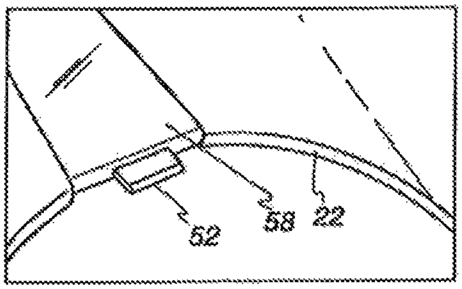
FIG. 17 illustrates a enlarged perspective view from below of a portion of the lens of FIG. 15 according to an embodiment of the disclosure.
Figure 18:
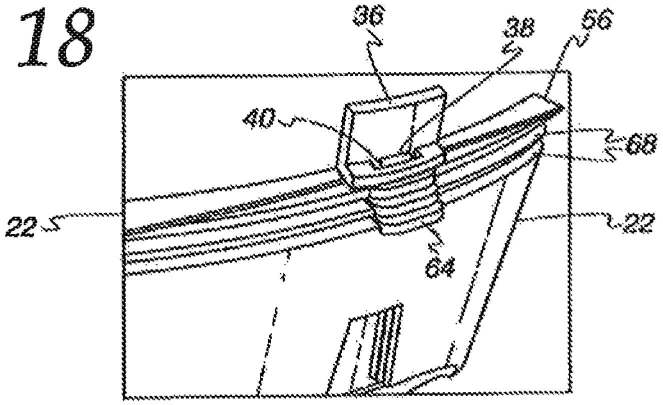
FIG. 18 illustrates a enlarged perspective view from above of a portion of the cartridge of FIG. 1 according to an embodiment of the disclosure.
Figure 19:
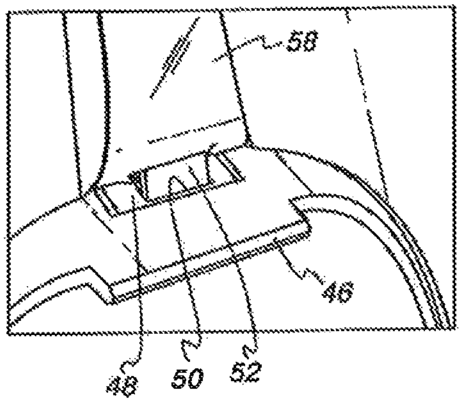
FIG. 19 illustrates a enlarged perspective view from the front showing a portion of the cartridge of FIG. 1 according to an embodiment of the disclosure.
Figure 20:
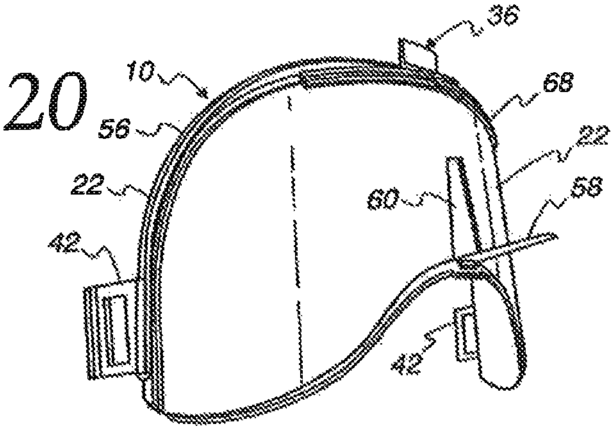
FIG. 20 illustrates a perspective view from the front and side of the cartridge of FIG. 1 according to an embodiment of the disclosure.

FIGS. 12-20 further illustrate the embodiment of the lens cartridge 10 comprising pull tabs 58 attached to the lower portion of the lenses 22, wherein like reference numbers indicate similar features and/or components. FIG. 12 shows a front view of the cartridge 10 described in FIG. 1; FIG. 13 shows a bottom view of the same cartridge 10 taken along the line 13-13 in FIG. 12; and FIG. 14 shows a cross-sectional view of the same cartridge 10 taken along the line 14-14 in FIG. 12. FIG. 14 is similar to FIG. 3 but shows only the elements of the lens cartridge 10. FIGS. 15-17 show different views and aspects of a single replaceable lens 22, while FIGS. 18-20 show different views and aspects of an assembled lens cartridge 10 comprising a plurality of replaceable lenses 22 in a stacked arrangement.

Figure 21:
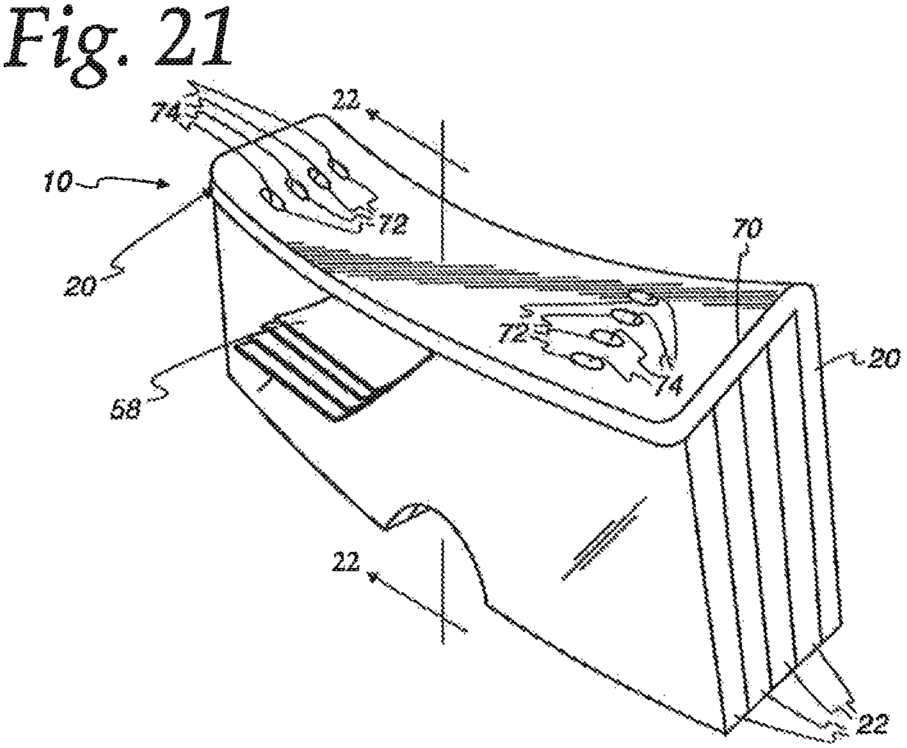
FIG. 21 illustrates a somewhat diagrammatic perspective view from the front and above of an alternate embodiment of the lens cartridge according to an embodiment of the disclosure.
Figure 22:
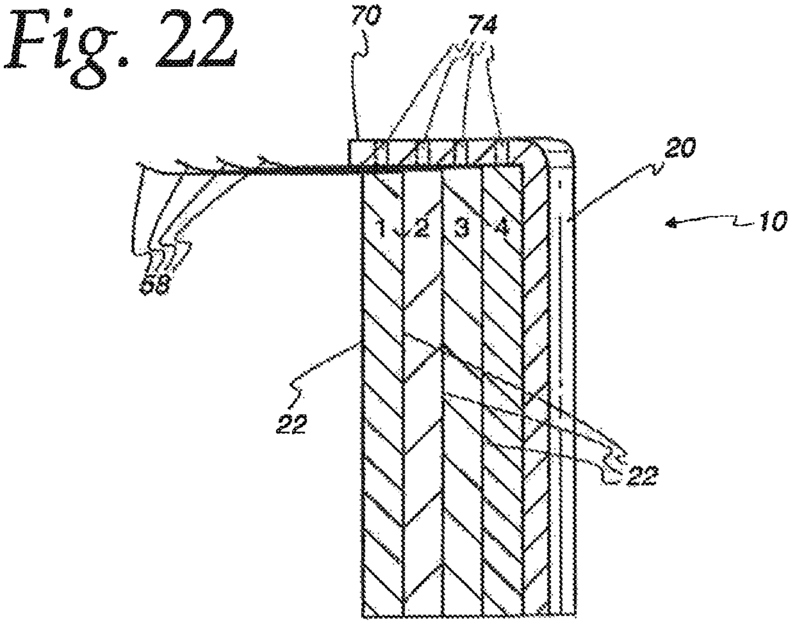
FIG. 22 illustrates a partial section view taken along line 22-22 in FIG. 21 according to an embodiment of the disclosure.
Figure 25:
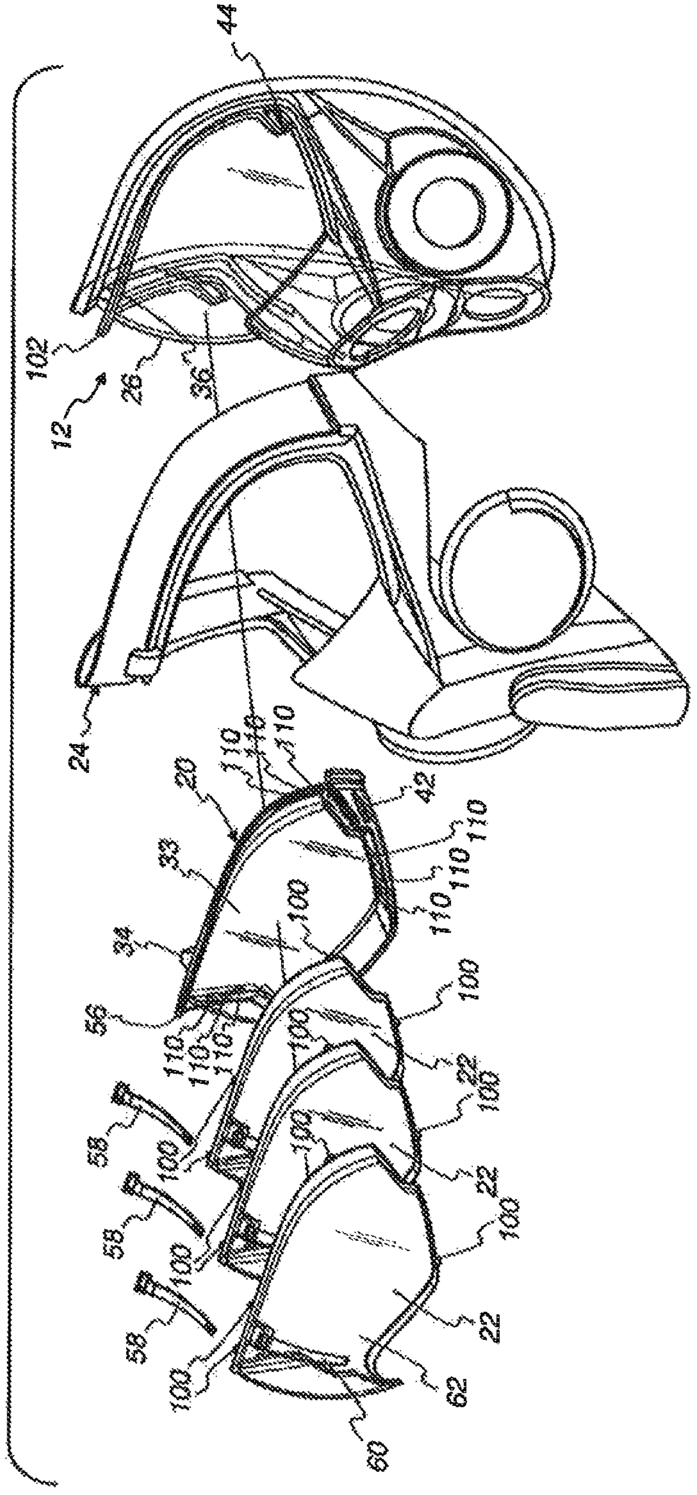
FIG. 25 illustrates a exploded perspective view from the front of the respirator of FIGS. 23A and 23B according to an embodiment of the disclosure.

FIGS. 21 and 22 illustrate alternate embodiment of the cartridge 10 wherein the carrier 20 has an L-shaped cross-section with a lip 70 that extends forwardly and includes a number of tab receiving openings 72 that receive mount tabs 74 formed on each of the lenses 22. This mount structure replaces the teeth 34, 40 and 52, slots 38 and 64, openings 50, blade 48, and bridge 46 of the embodiment illustrated in FIGS. 1-20. This embodiment also differs from the previously described embodiment in that the pull tab 58 is attached to and extends in cantilevered fashion from an upper portion of each lens 22, rather than from a lower central portion as in FIGS. 1-20.

FIGS. 23A-33 illustrate another embodiment for the lenses 22 and lens cartridge 10 together with a respirator 14 for that embodiment, with like reference numbers indicating similar features and/or components.

As with the prior described embodiments, the embodiment of FIGS. 23A-33 is mostly dedicated to the shipyard industry, but could be suitable for different types of construction site where sandblasting/shot blasting (typically with some form of grit) is performed, and could also be extended to other industries such as welding, painting, oil rig and any other activities that require optic protection that gets damaged by different media (dirt, oil, paint, etc.).

As with the prior described concepts, the concept is to make the replacement lens cartridge 10 with molded plastic (for example, polycarbonate, TPU, acrylic, etc.) suitable for optic purposes. Because of the process and material, this concept is also a cost effective system. Density of resins, such as polycarbonate, is half of the glass density which brings down the weight considerably.

The embodiment of FIGS. 23A-33 differs from the embodiment of FIGS. 1-20 in that it has eliminated the cantilevered blade 48 and openings 50 on the carrier 20, the corresponding tooth 52 on each of the lenses 22, the top tooth 40 on each of the lenses 22 and the corresponding slot 64 on each of the lenses 22 and has provided for a different means of releasably securing each of the lenses 22 to the carrier 20, as will be discussed more fully below.

As with the prior embodiments, the cartridge 10 comprises a carrier 20 and multiple disposable lenses 22 (typically 3 or 4 such lenses). Because the cartridge 10 is molded, the lenses 22 are no longer limited by flat surfaces, and may be cylindrical lens, spherical lens or tonic lens. With those curvatures its possible to offer more peripheral view. For example, in one embodiment, the curved shape of the lenses 22 may allow for a field of vision of between about 100° and about 170°.

Figure 30:
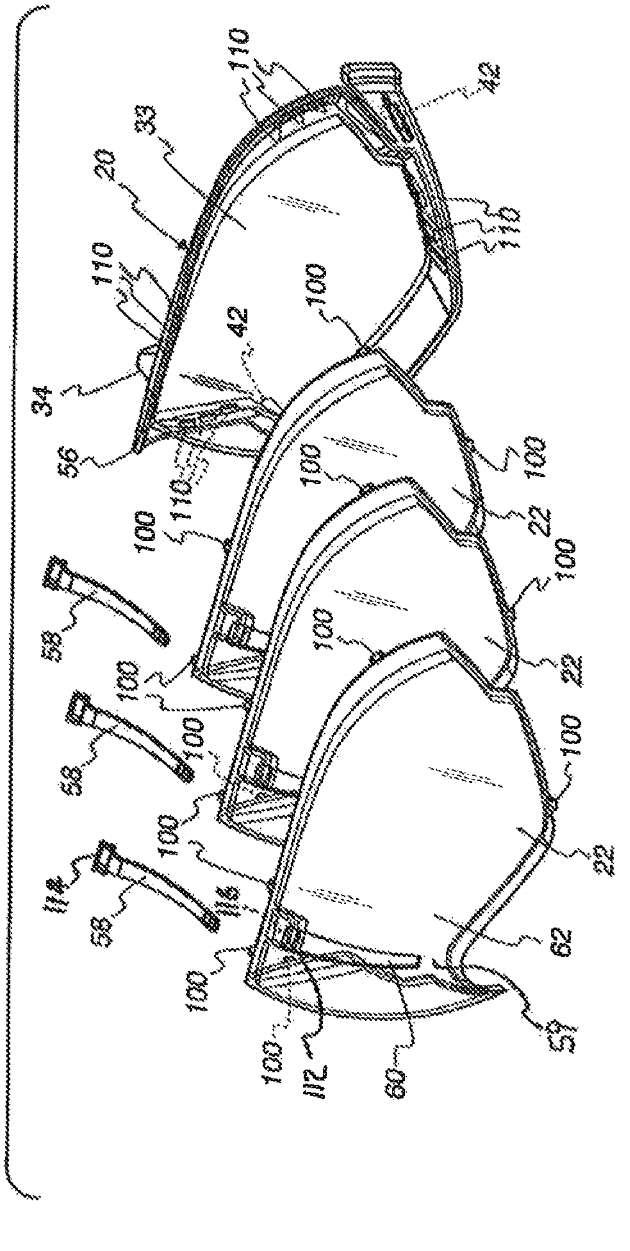
FIG. 30 illustrates an enlarged exploded view of the cartridge and lenses of FIGS. 23A and 23B according to an embodiment of the disclosure.

While each lens inside the carrier 20 can be identical, if overwhelming distortion occurs by stacking the lenses 22 it would be possible to make each of them slightly different to correct distortion made by the previous lens 22 in the cartridge 10. More specifically, as best seen in FIG. 30, the fixed lens 33 of the carrier 20 and each of the replacement or disposable lens 22 (1, 2 and 3) has its own inside and outside spherical radius to correct distortion/deformation that was created by the previous one. Each replacement lens 22 is different in size and has different positions for a plurality of catches in the form of retaining hooks, tabs, or projections 100 formed on the perimeter of each lens 22 that clip into a corresponding set of catches in the form of recesses, openings, or grooves 110 formed into the peripheral lip 56 of the carrier 20. This will ensure that replacement lenses 22 are in the right order in the carrier 20 to provide optimal optics. The goal is to obtain almost no distortion with multiple layers of lenses 22.

Figure 26:
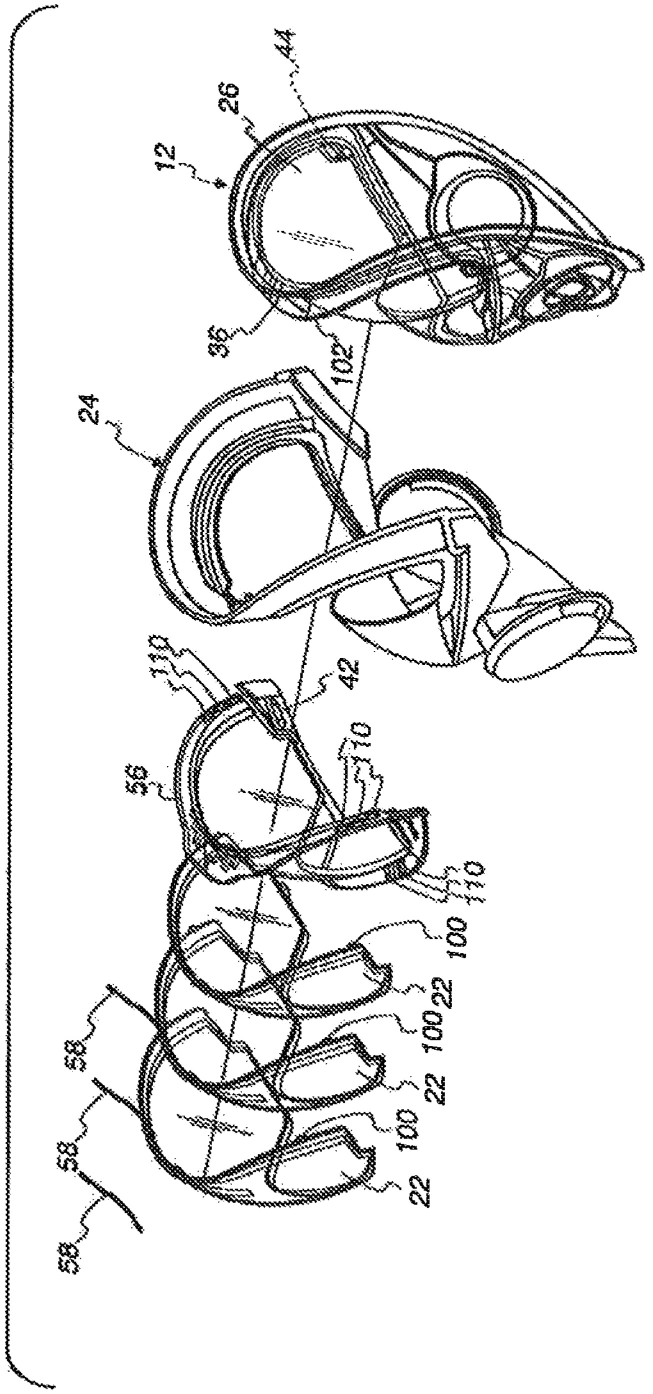
FIG. 26 illustrates a exploded perspective view from the rear of the respirator of FIGS. 23A and 23B according to an embodiment of the disclosure.
Figure 27:
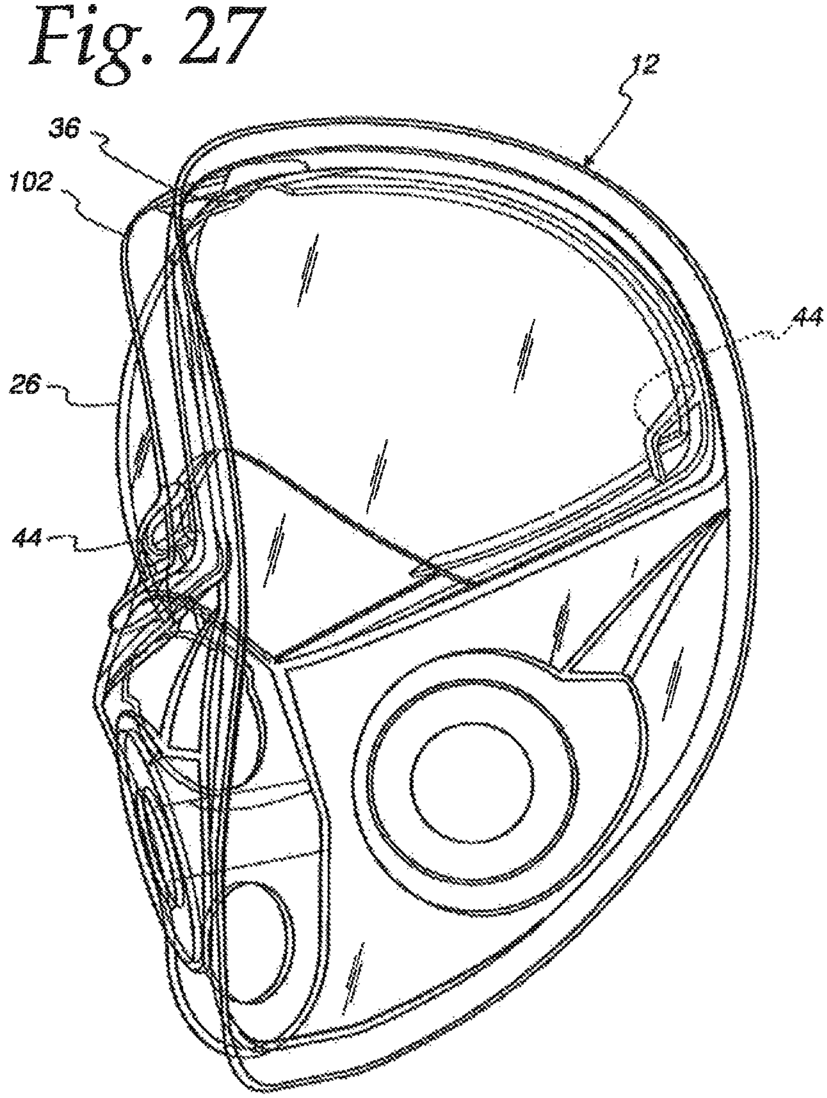
FIG. 27 illustrates a enlarged exploded rear view of selected components of the respirator of FIGS. 23A and 23B according to an embodiment of the disclosure.
Figure 28:
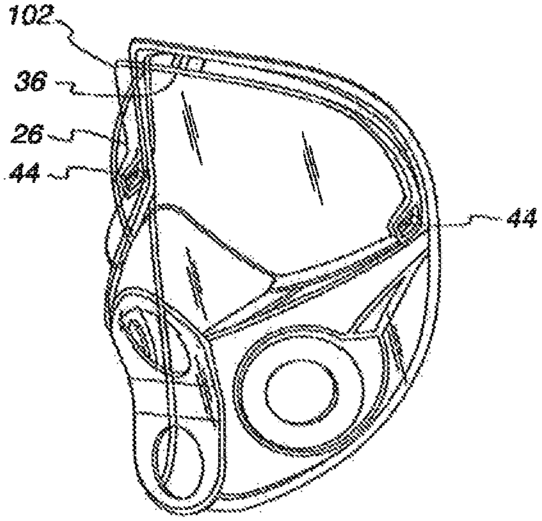
FIG. 28 illustrates a perspective view from the front and side of the respirator of FIGS. 23A and 23B with a protective shield removed according to an embodiment of the disclosure.
Figure 29:
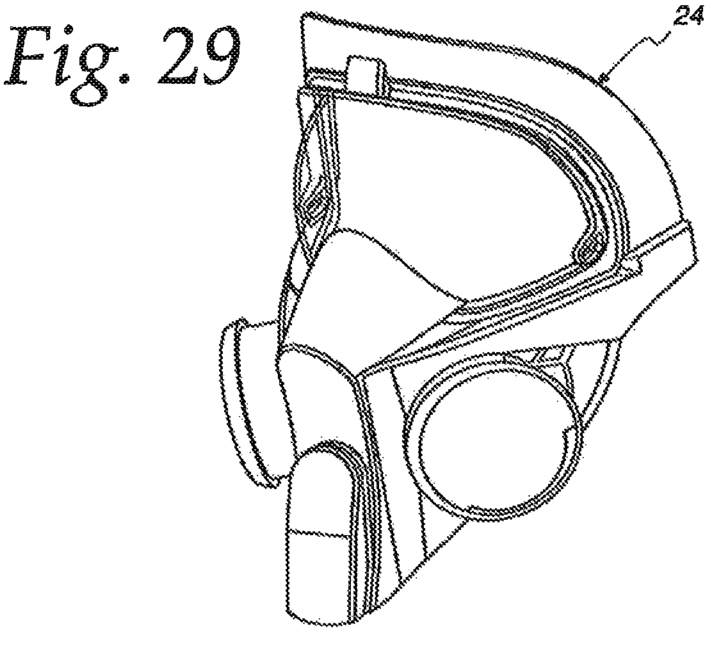
FIG. 29 illustrates a perspective view similar to FIG. 28 but showing the protective shield in place according to an embodiment of the disclosure.
Figure 31:
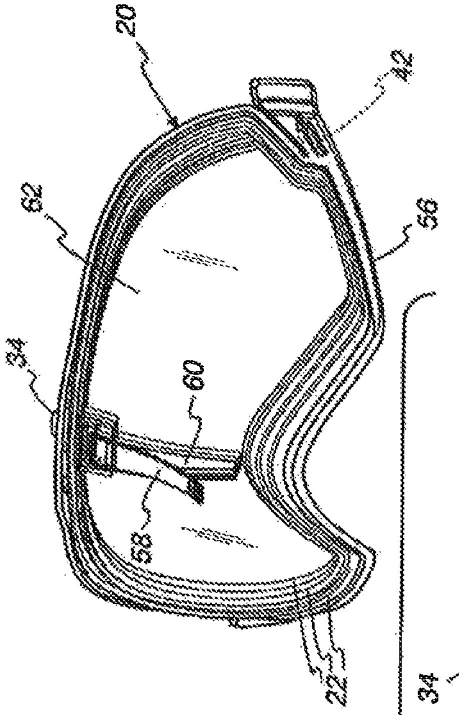
FIG. 31 illustrates an assembled perspective view of the lens cartridge of FIGS. 23A and 23B and FIG. 30 according to an embodiment of the disclosure.
Figure 32A:
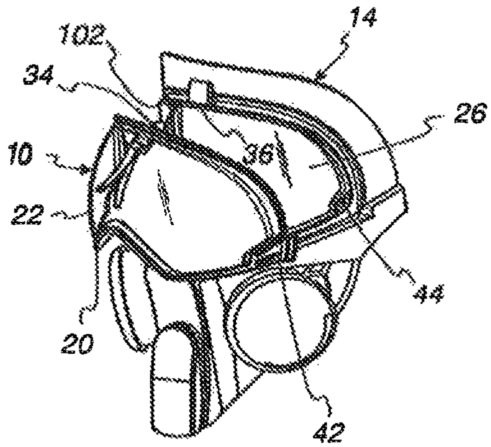
FIGS. 32A-32C illustrate a sequence of views illustrating the mounting of the lens cartridge to the respirator of FIGS. 23A and 23B according to an embodiment of the disclosure.
Figure 32B:
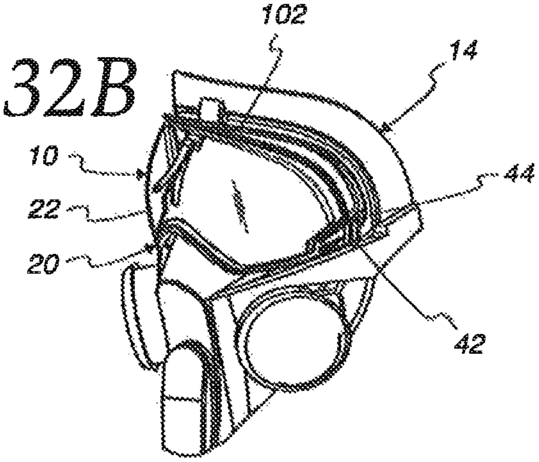
Figure 32C:
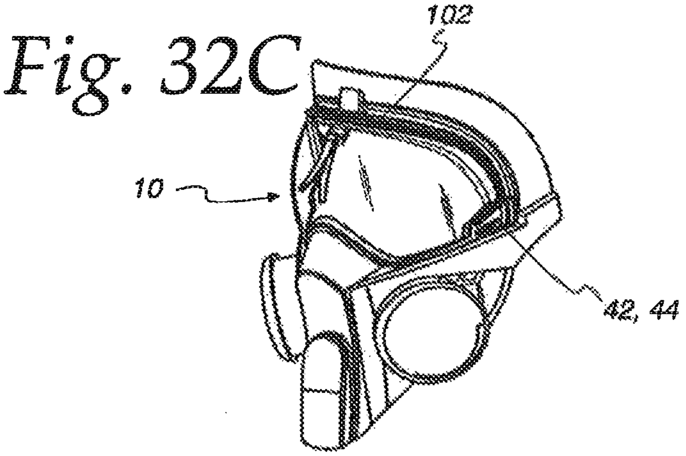
Figure 33:
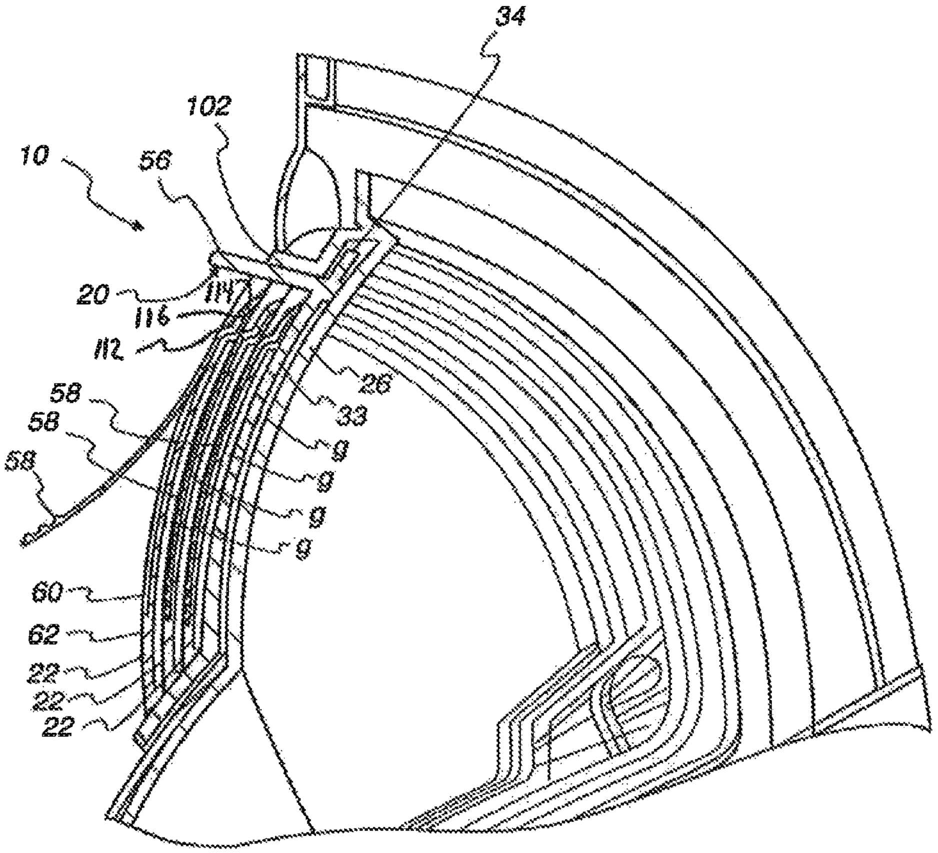
FIG. 33 illustrates an enlarged sectional view of the lens cartridge and respirator of FIGS. 23A and 238 according to an embodiment of the disclosure.

As best seen in FIGS. 32A-32C, when the lens cartridge 10 is mounted on the respirator 14, it leans on a protective rim 102 that is molded on the base lens 26 of the face mask 12 of the respirator 14. As seen in FIGS. 26 and 29, there is a rubber/TPE piece or shield 24 that covers portions of the base lens 26 and the filter of the respirator 14. As best seen in FIG. 33, between the base lens 26 and the lens 33 carrier 20 there is a gap g of air that plays a role in the optic correction. There is also a gap g of air between each lens 22 to allow geometric compensation.

As best seen in FIGS. 32A-32C, the carrier 20 holds the stack of lenses 22 together and provides means to attach the cartridge 10 on the respirator 14. Its lens 33 is also the last layer of protection of the cartridge 10 such that at all times, the user has at least two layers of eye protection (for example, provided by the base lens 26 of the face mask 12 and the fixed lens 33 of the carrier 20). In an embodiment, the carrier 20 has a top tooth 34 that is inserted into a clamp or slot 36 in the rim 102 on the respirator 14. There is a catch in the form of a projection or hook 42 on each side of the carrier 20 to secure the lens cartridge 10 on the respirator 14 by snap engagement with catches in the form of indents or recesses 44 on the face mask 12. As previously discussed, each replacement lens 22 is retained by the catches 100 on its perimeter that are inserted in the corresponding carrier catches 110.

As best seen in FIGS. 30 and 33, each lens 22 in the cartridge 10 has a transparent or opaque pull tab 58 in the center for removal of the used lens 22. This tab 58 can be snapped in a secondary operation by inserting each tab 58 through a slot 112 in the corresponding lens 22 until a thickened end 114 of the tab 58 is received in an indent 116 on the back face of the lens 22. There is a recess 60 on the front surface of the lens 22 to receive the folded tab 58 to avoid creating any unwanted gaps between the lenses 22.

Figure 34:
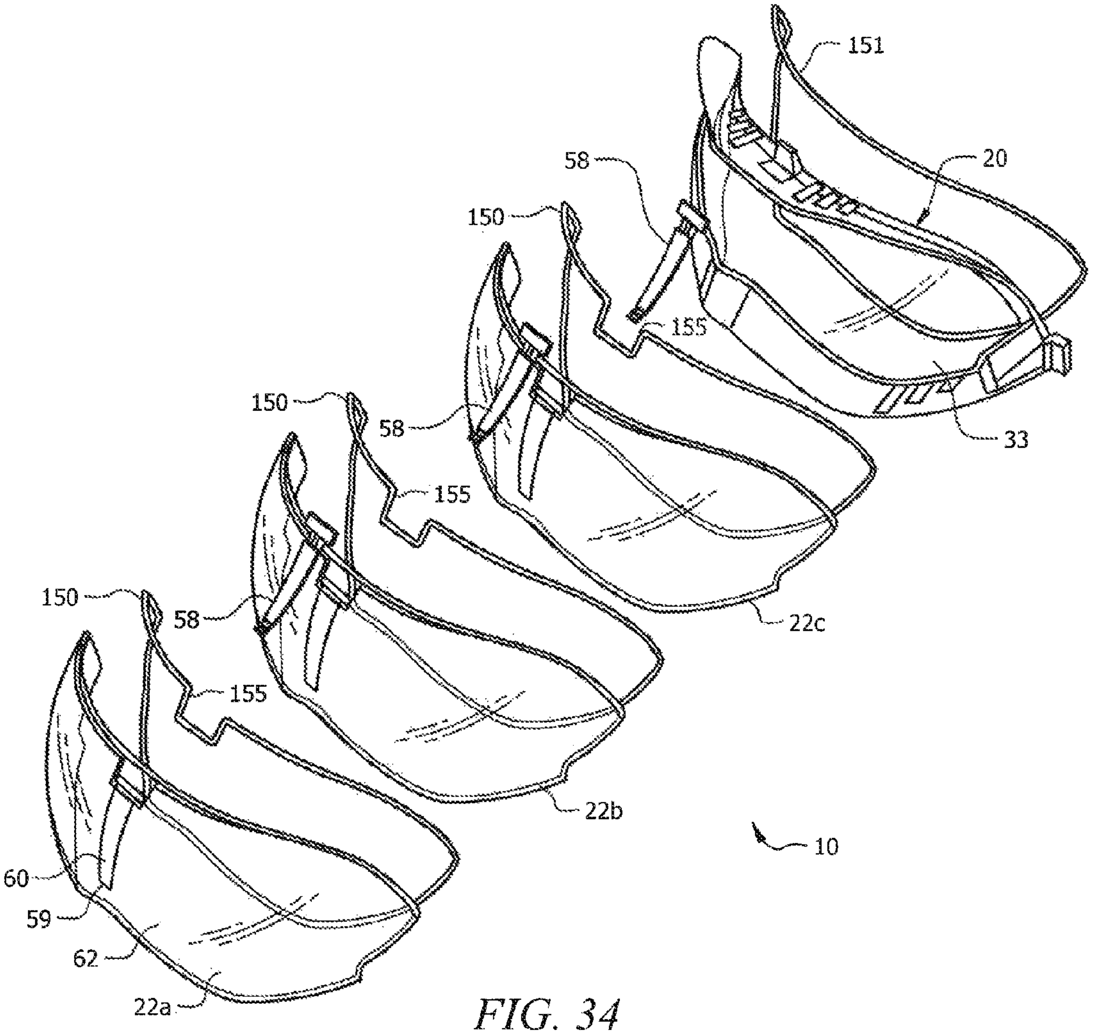
FIG. 34 illustrates an alternative embodiment of a lens cartridge comprising gaskets therein between each of the lenses in the cartridge according to an embodiment of the disclosure.
Figure 35:
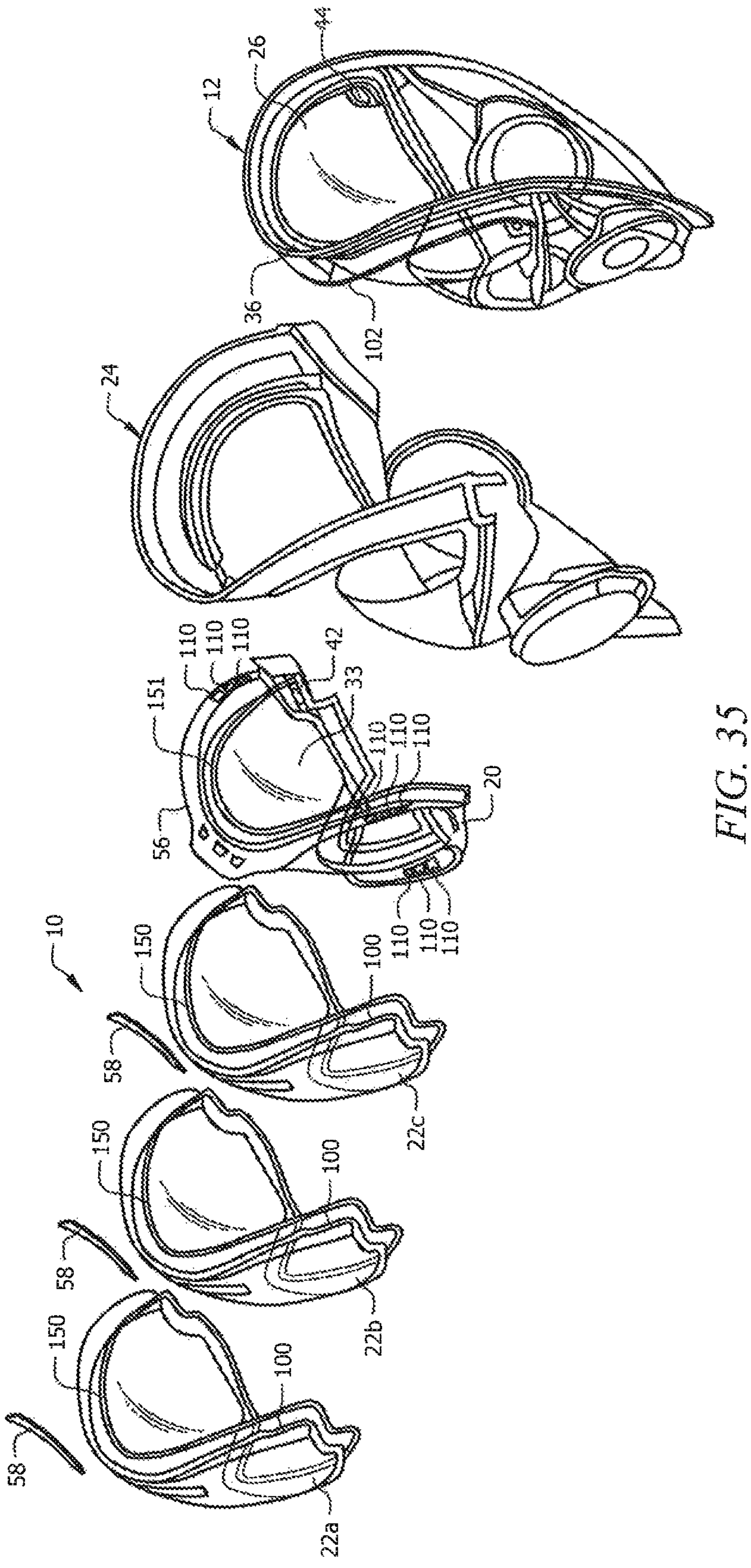
FIG. 35 illustrates another view of an embodiment of a lens cartridge comprising gaskets therein between each of the lenses in the cartridge according to an embodiment of the disclosure.

FIGS. 34-35 illustrate an alternative embodiment in which the lens cartridge 10 may additionally comprise gaskets (or seals) 150 located between each of the removable lenses 22*a*, 22*b*, and 22*c* and also possibly located between the lens 22*c* and the carrier 20. Additionally, a gasket 151 may be located between the fixed lens 33 of the carrier 20 and the base lens 26 of the face mask 12 in some embodiments. The gaskets 150 may be shaped to fit against a back surface or edge of each lens 22*a*, 22*b*, and 22*c* and may be operable to seal the air gap g (as shown in FIG. 33) between each of the lenses from the entrance of particulates or other media in the air. The particulates may for example come from the abrasive blasting grit material being used by a wearer of the face mask 12. In an embodiment, the gaskets 150 may be designed to adhere or attach to the back edge or surface of a first lens 22*a* and seal to the front edge or surface of a second lens 22*b* and/or the fixed lens 33 of the carrier 20 when the multiple lenses are in place in the cartridge 10. The material of the gasket 150 may be such that a seal is formed between the lenses 22*a*, 22*b*, and 22*c* while allowing for the gasket 150 to be removed along with a corresponding removable lens 22*a*, 22*b*, and 22*c* when necessary.

The gaskets 150 may be designed such that when the first removable lens 22*a* is removed from the cartridge 10, the corresponding gasket 150 remains attached, affixed or adhered to the first lens 22*a* and is completely released from the seal with the second lens 22*b* and may in some embodiments release the seal with the second lens 22*h* substantially without any residue, adhesive, or gasket material remaining on the surface or edge of the second lens 22*b*. Similarly, the gasket 151 may be attached or adhered to the back edge or surface of the fixed lens 33 of the carrier 20 and may be designed such that a seal is formed between the fixed lens 33 and the base lens 26 of the face mask 12, while allowing for the gasket 151 to be removed along with the removable cartridge 10 when necessary. In other words, when the cartridge 10 (and therefore the carrier 20) is removed from the face mask 12, the gasket 151 may remain attached to the carrier 20 and be completely released from the seal with the base lens 26 and in some embodiments may release the seal without any residue, adhesive, or gasket material remaining on the surface or edge of the base lens 26.

In one embodiment, the gaskets 150 and 151 may comprise the same material or different materials, and in one embodiment the gaskets 150 and 151 may comprise a gasket material provided by Dymax™ GA-105. In an embodiment, the material of the gasket may comprise a soft, sticky material, for example an adhesive, and may in some embodiments comprise acrylated urethane, which may have the appearance of a clear translucent gel. In an embodiment where the gasket material may be uncured (that is before the gasket shape is formed) the material may have a density of about 1 g/mL, and may have a nominal viscosity of about 40,000 cP. As used herein, cured means solidifying material by exposing it to heat, air, time, or UV rays, for example. In an embodiment, the gasket material may reach a cured state by exposure to visible and/or UV light, and the cured gasket material may have hardness of about 70 Durometer and modulus of elasticity of about 0.2 MPa. When cured and in place on the lens, the gasket material may comprise a tackiness that allows for removal of the gasket with the first lens (such that the gasket is securely attached or affixed to the hack surface of the first lens) without leaving residue or gasket material on the second lens. The gasket material may also comprise a thickness of about 0.05 to 0.1 inch when in place on the lens, wherein the thickness may measure the distance the gasket extends from the surface of the lens, and the gasket material may comprise a width of about 0.05 to 0.1 inch when in place on the lens.

In one embodiment, an adhesive may be used between the gasket 150 and the back edge or surface of the lenses 22*a*, 22*b*, and 22*c* to ensure that the gasket remains adhered to the first lens 22*a* when it is removed and does not remain sealed to the second lens 22*b*, and similarly to ensure that the gasket remains adhered to the second lens 22*h* when it is removed and does not remain sealed to the third lens 22*c*, etc. In another embodiment, the material of the gasket 150 may be adhesive itself, typically with one side (i.e. the side in contact with the back edge or surface of the lens 22*a*, 22*b*, and 22*c*) having a higher adhesive property/quality than the other side of the gasket 150, allowing for complete removal of the gasket 150 with the lens 22*a*, 22*b*, and 22*c*. Similarly, the material of the gasket 151 may be designed such that one side (i.e. the side in contact with the back edge or surface of the fixed lens 33 of the carrier 20) has higher adhesive property/quality than the other side of the gasket 151, allowing for complete removal of the gasket 151 with the fixed lens 33 of the carrier 20. In some embodiment adhesive gasket may form a secure attachment to the first (or top) lens by being place on the first lens and cured before the gasket contacts the second (or bottom) lens. By curing the adhesive gasket material prior to contact with the second lens, a removable seal may be formed between the gasket and the second lens (while the gasket is securely affixed to the first lens).

In an embodiment shown in FIG. 34, the shape of the gaskets 150 may match the shape of the corresponding lenses 22*a*, 22*b*, and 22*c*, for example, such that the gaskets 150 align approximately with the edges of the lenses 22*a*, 22*b*, and 22*c*. In an embodiment, the shape of the gaskets 150 may include a notch 15 to avoid interference by the gasket with the removal mechanism of the lenses 22*a*, 22*b*, and 22*c* with the tabs 58. In an embodiment, the shape of the gasket 151 may match the shape of the base lens 33 of the carrier 20, such that the gasket 151 aligns with the edges of the base lens 33. In an embodiment wherein the lenses 22*a*, 22*b*, and 22*c* and the fixed lens 33 comprise a curved shape, the gaskets 150 and 151 may comprise a curved shape so as to fully interact with the edges or surfaces of the lenses 22*a*, 22*b*, and 22*c* and the fixed lens 33 in such a fashion as to seal the entire edge or surface of the lenses 22*a*, 22*b*, and 22*c*, the fixed lens 33, and the base lens 26 of the face mask 12 from the entrance of particulates or other media in the air.

Alternative embodiments of means for sealing between the sacrificial lenses (to minimize entry of grit between lenses while allowing each lens to be removed as needed, for example with gloved hand(s)) may be understood by persons of interest based on the disclosure herein. For example, rather than (or in addition to) using adhesive gasket(s) between lenses, overmolding and/or two shot molding of rubber-like material on the lenses might be used, a d/or overmolding and/or two shot molding of rubber-like material on the magazine (cartridge) might be used. These and other sealing means may be available for specific embodiments.

Another embodiment of the disclosure may comprise a method of making or assembling a removable lens cartridge comprised of removable lenses, wherein a plurality of lenses may be provided, wherein the lenses may be formed of molded polycarbonate plastic material. Gasket material may then be placed on the back surface of each of the plurality of lenses, and may be cured (for example using visible and/or UV light) such that the gasket material becomes affixed to the back surface of each of the removable lenses. The material of the gasket may be such that, after the material is cured it remains sticky or tacky enough to form a seal with another surface, such as that of another lens. In an embodiment, the placing of the gasket material on the back surface of the lenses may be performed automatically, such as by a robot for example. Additionally, a carrier may be provided operable to hold the plurality of removable lenses in a stacked arrangement, wherein the carrier may comprise a fixed lens and may be at least partially formed of molded polycarbonate plastic material. After the gasket material is placed on the back surface of the removable lenses and is cured, the lenses may be placed in the stacked arrangement within the carrier. In an embodiment, a first removable lens may be placed within the carrier, and the gasket material affixed to the back surface of the removable lens may contact the front surface of the fixed lens of the carrier and may form a seal between the fixed lens and the removable lens. Then, a second removable lens may be placed within the carrier and the gasket material affixed to the back surface of the second removable lens may contact the front surface of the first removable lens and may form a seal between the two removable lenses. This method may be repeated until the carrier holds the number of removable lenses it is designed to hold (typically three or four lenses), wherein each of the plurality of removable lenses located within the carrier may be sealed to one another with the gasket material. In an alternative embodiment, the lenses may all be attached to one another, creating seals between each of the lenses, and then placed within the carrier. Additionally, gasket material may be placed on the back surface of the fixed lens of the carrier and cured so that the gasket material becomes affixed to the back surface of the fixed lens. The carrier may then be placed on a face mask of a respirator, wherein the face mask may comprise a base lens, and a seal may be formed between the front surface of the base lens of the face mask and the back surface of the fixed lens of the carrier.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A replaceable lens cartridge for use with a face mask comprising:

a plurality of removable lenses;

a carrier mounting the lenses in a stacked arrangement, wherein the stacked arrangement comprises gaps between the lenses; and a plurality of gaskets located between the lenses in the stacked arrangement, wherein the gaskets are operable to seal the gaps between the lenses.

2. The lens cartridge of claim 1 wherein each gasket comprises a shape corresponding approximately to an outline of a corresponding lens and is located in proximity to edges of adjacent lenses.

3. The lens cartridge of claim 1 wherein the gaskets comprise an adhesive material that attaches securely to a back surface of a first lens and seals to a front surface of a second lens.

4. The lens cartridge of claim 3 wherein a seal of a gasket to a corresponding front surface of the second lens is removable, such that when the first lens is removed from the cartridge, the corresponding gasket that is attached to the back surface of the first lens is completely removed as well and remains attached to the back surface of the first lens.

5. The lens cartridge of claim 4 wherein when the first lens is removed from the cartridge, the gasket is completely removed from sealing with the front surface of the second lens, without leaving any portion of the gasket material on the front surface of the second lens.

6. The lens cartridge of claim 1 wherein each lens comprises a plurality of catches and the carrier comprises a corresponding plurality of catches to receive the catches of the lenses to form the stacked arrangement.

7. The lens cartridge of claim 6 wherein the plurality of catches on each lens comprises at least four projections extending from the perimeter of the lens, and wherein the corresponding plurality of catches on the carrier comprises a matching number of reliefs on the carrier, each relief receiving one of the projections.

8. The lens cartridge of claim 6 wherein the carrier further comprises a peripheral lip that extends over perimeters of the lenses mounted in the stacked arrangement on the carrier, and the plurality of catches of the carrier is formed in the peripheral lip of the carrier.

9. The lens cartridge of claim 1 wherein the carrier further comprises a fixed lens underlying the lenses mounted in stacked arrangement on the carrier, and the lens cartridge further comprises a gasket located behind the fixed lens operable to seal between the fixed lens of the carrier and the face mask.

10. The lens cartridge of claim 9 wherein the carrier further comprises a plurality of mount catches for engagement with the face mask.

11. The lens cartridge of claim 10 wherein the face mask comprises a base lens and the gasket located behind the fixed lens seals between the fixed lens of the carrier and the base lens of the face mask.

12. The lens cartridge of claim 9 wherein the plurality of lenses and the fixed lens of the carrier comprise a curved shape.

13. The lens cartridge of claim 1 wherein the plurality of lenses comprises a curved shape.

14. The lens cartridge of claim 13 wherein the curved shape of the lenses allows for a field of vision of between about 100° and about 170°.

15. The lens cartridge of claim 13 wherein the gaskets comprise a curved shape corresponding to the curved shape of the removable lenses and the fixed lens.

16. The lens cartridge of claim 1 wherein the plurality of lenses is formed of molded polycarbonate plastic material.

17. A replaceable lens cartridge for use with a respirator face mask for use during blasting with grit comprising:

a plurality of removable lenses formed of molded plastic;

a carrier mounting the lenses in a stacked arrangement, wherein the stacked arrangement comprises gaps between the lenses; and a plurality of gaskets located between the lenses in the stacked arrangement, wherein the gaskets are operable to seal the gaps between the lenses sufficiently to prevent grit from entering between the lenses;

wherein each gasket comprises an adhesive material between a corresponding top lens and bottom lens, wherein the gasket is affixed to a back surface of the top lens and seals removably to a front surface of the bottom lens.

18. The lens cartridge of claim 17 wherein, upon removal of the top lens from the cartridge, the corresponding gasket that is attached to the back surface of the top lens is completely removed and remains affixed to the back surface of the top lens, without leaving any significant portion of the gasket material on the front surface of the bottom lens.

19. The lens cartridge of claim 17 further comprising a plurality of pull tabs, each tab corresponding to one of the lenses, wherein the tab is centered on the lens and attached to the lens to allow for removal of the lens from the carrier when the tab is pulled, wherein each lens includes a recess underlying the pull tab to receive the pull tab and prevent unwanted interference between the pull tab and any adjacent lens.

20. The lens cartridge of claim 19 wherein the gaskets comprise a shape corresponding approximately to a perimeter outline of the lenses which includes a notch to avoid interference with the pull tabs.

* * * * *

UNITED STATES PATENT AND TRADEMARK OFFICE
CERTIFICATE OF CORRECTION

PATENT NO. : 8,873,170 B2
APPLICATION NO. : 13/683661
DATED : October 28, 2014
INVENTOR(S) : Swapnil Gopal Patil et al.

It is certified that error appears in the above-identified patent and that said Letters Patent is hereby corrected as shown below:

In the Specification

Column 6, Line 19: “Its” should be “It’s”

Column 3, Line 21: “parts.” should be “parts:”

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*